US010001453B2

(12) United States Patent
Pagani et al.

(10) Patent No.: US 10,001,453 B2
(45) Date of Patent: Jun. 19, 2018

(54) INTEGRATED ELECTRONIC DEVICE FOR MONITORING HUMIDITY AND/OR CORROSION

(71) Applicant: STMICROELECTRONICS S.r.l., Agrate Brianza (MB) (IT)

(72) Inventors: Alberto Pagani, Nova Milanese (IT); Bruno Murari, Monza (IT)

(73) Assignee: STMICROELECTRONICS S.R.L., Agrate Brianza (MB) (IT)

( * ) Notice: Subject to any disclaimer, the term of this patent is extended or adjusted under 35 U.S.C. 154(b) by 3 days.

(21) Appl. No.: 14/781,104

(22) PCT Filed: Mar. 28, 2014

(86) PCT No.: PCT/IB2014/060249
§ 371 (c)(1),
(2) Date: Sep. 29, 2015

(87) PCT Pub. No.: WO2014/155348
PCT Pub. Date: Oct. 2, 2014

(65) Prior Publication Data
US 2016/0041113 A1 Feb. 11, 2016

(30) Foreign Application Priority Data
Mar. 29, 2013 (IT) .............................. MI2013A0484

(51) Int. Cl.
*G01N 27/22* (2006.01)
*G01N 17/00* (2006.01)
*G01N 17/04* (2006.01)

(52) U.S. Cl.
CPC ........... *G01N 27/223* (2013.01); *G01N 17/04* (2013.01)

(58) Field of Classification Search
CPC .............................. G01N 27/04; G01N 27/048
See application file for complete search history.

(56) References Cited

U.S. PATENT DOCUMENTS 4,632,879 A * 12/1986 Tanaka ................. G01N 27/121
252/194

5,331,287 A * 7/1994 Yamagishi ........... G01N 27/121
204/421

(Continued)

FOREIGN PATENT DOCUMENTS

CN 1455250 11/2003
CN 102249681 11/2011
(Continued)

OTHER PUBLICATIONS

Fuchs et al. Using Capacitive Sensing to Determine the Moisture Content of Wood Pellets Investigations and Application International Journal on Smart Sensing and Intelligent Systems, vol. 2, No. 2, Jun. 2009; pp. 293-308.

*Primary Examiner* — Noam Reisner
(74) *Attorney, Agent, or Firm* — Slater Matsil, LLP

(57) ABSTRACT

An integrated electronic device 1 for detecting at least one parameter related to humidity and/or presence of water and/or acidity/basicity of an environment surrounding the device is described. Such device 1 comprises a separation layer 14 from the surrounding environment, comprising at least one portion of insulating material 14, and further comprises a first conductive member 11 and a second conductive member 12, made of an electrically conductive material, arranged inside the separation layer 14, with respect to the surrounding environment, and separated from the surrounding environment by the separation layer 14. The device 1 also comprises a measurement module 15, having two measurement terminals 151, 152, electrically connected with the first 11 and the second 12 conductive members, respectively; the measurement module 15 is configured to provide an electric potential difference between the first 11 and the second 12 conductive members. The device 1 further comprises electrode means 13, configured to act as an electrode, arranged outside of the separation layer 14, with respect to the first 11 and the second 12 conductive members; the electrode means 13 are arranged so as to form, with the first 11 and the second 12 conductive members, an electromagnetic circuit having an electromagnetic circuit overall impedance variable based upon the exposure to environmental conditions with a variable level of humidity and/or acidity/basicity. The measurement module 15 is configured to measure the electromagnetic circuit overall impedance, which is present between the measurement terminals 151, 152, and to determine the at least one (Continued)

parameter to be detected, based on the overall impedance measured.

16 Claims, 11 Drawing Sheets

(56) References Cited

U.S. PATENT DOCUMENTS

| | | | |
|---|---|---|---|
| 6,373,263 | B1 | 4/2002 | Netzer |
| 8,079,256 | B2 | 12/2011 | Langenbacher et al. |
| 2003/0179805 | A1 | 9/2003 | Hamamoto et al. |
| 2009/0033467 | A1 | 2/2009 | Finocchiaro et al. |
| 2009/0141767 | A1 | 6/2009 | Cummins |
| 2010/0192688 | A1* | 8/2010 | Humbert ............... G01N 17/04 73/335.03 |
| 2011/0221456 | A1 | 9/2011 | Fronheiser et al. |
| 2012/0286804 | A1* | 11/2012 | Kato ................... G01N 33/383 324/649 |

FOREIGN PATENT DOCUMENTS

| | | |
|---|---|---|
| DE | 10 2008 039 857 | 4/2010 |
| WO | 01/81931 | 11/2001 |
| WO | 2007/036922 | 4/2007 |
| WO | 2009/016594 | 2/2009 |
| WO | 2012084295 | 6/2012 |

\* cited by examiner

INTEGRATED ELECTRONIC DEVICE FOR MONITORING HUMIDITY AND/OR CORROSION

TECHNOLOGICAL BACKGROUND OF THE INVENTION

Field of Application

The present invention relates to integrated electronic devices for detecting one or more parameters relating to the presence of water, humidity, acidity/basicity of an environment surrounding the device. A monitoring system, and a method for detecting such parameters are also comprised in the invention, such system and method using the above-mentioned device.

Description of the Prior Art

In the field of monitoring an environment around a given monitoring point, it is very important to take into account parameters such as humidity and acidity/basicity.

If there are structures or parts of structure made of metal, in the environment to be monitored, it is also important to carry out an assessment of the state of corrosion of such metal parts.

Monitoring of solid structures, such as load-bearing structures of bridges, or also of buildings, tunnels, railways, dams, embankments, underground structures of city underground railways, etc., can be considered as an application example significant for illustrative purposes, however not being limiting. In particular, structures in building material, for example reinforced concrete, composed of concrete reinforced with metal rods can be considered.

In this context, devices and systems for monitoring different parameters, relating to forces or temperature, are known. For example, the international patent application WO 2012/084295, by the Applicant, discloses a device for monitoring, inside a solid structure, a mechanical stress and/or pressure and/or temperature, comprising an integrated detection module, in which at least one integrated sensor and the relative circuitry are included, as well as electromagnetic means for the communication to and from the outside. In WO 2012/084295, the integrated detection module comprises a passivating layer that completely coats the integrated sensor and the relative circuitry, to ensure robustness and a long operative lifetime; however, this feature prevents such devices from detecting humidity and/or acidity/basicity. The importance to detect parameters such as humidity and/or acidity/basicity is crucial, in view of a meaningful and reliable monitoring.

Designers and maintenance technicians of structures to be monitored need to assess the evolution of the degradation due to the presence of water and/or humidity. In fact, the phenomena that may cause such degradation are numerous.

As regards concrete, this is an artificial stone material composed of stone aggregates with different dimensions, referred to as inerts, joined by cement, which is an hydraulic binder, the activation of which occurs due to chemical reactions with water. Inerts have dimensions ranging from a few tenths of a millimeter to some tens of millimeters. The cement granules have a size ranging from 1 to 50 µm, and they fill the spaces that are present between the inerts, determining a solidified slurry, on the whole porous and permeable. The concrete can have different degrees of porosity and permeability, depending on its composition and the size of inerts and cement granules; however, a certain degree of porosity and permeability can be anyhow found.

Because of this fact, humidity and/or other atmospherical agents and/or water (which may in turn contain different chemical compounds in solution) penetrate into the concrete and may cause several chemical/physical phenomena, such as to degrade both the concrete, and the metal of the rods (i.e., the reinforcing steel or iron bars) present in the reinforced concrete. Among the main causes of degradation, the following ones can be mentioned.

Carbonation is due to the penetration of humidity, oxygen $O_2$ and carbon dioxide $CO_2$ into the cement. Such phenomenon does not involve a reduction of the robustness of the concrete, but it is very dangerous for the reinforcing iron bars. Usually, in the concrete, by virtue of the lime that is formed by hydration of the cement, the pH is strongly basic (12-14) and the iron bars are thus passivated and protected by such alkaline environment through the formation of a passivating film of iron oxide, adherent to the iron bars and not permeable, which prevents a further oxidation. However, when the outermost layer of the concrete structure, also referred to as "concrete cover", is penetrated by $CO_2$, lime is neutralized and calcium carbonate is formed, which decreases the pH, determining a more and more acid environment, and starting the corrosion of the iron when the pH has a value of about 8 or 7. Furthermore, the rust that is formed by the oxidation of the iron bars, causes a volume increase, determining a traction on the concrete, which may crack and even cause the release of the concrete cover layer due to the tensional load; the surfacing iron bars are thus exposed to a rapid corrosion that may cause the rapid degradation of the structure and compromise the stability thereof.

A sulphate etch occurs when the infiltrated water comprises sulphates, reacting with calcium hydrates, aluminates and silicates of the cement, thus forming gypsum, ettringite and thaumasite, thus causing bulging, cracks and releases in the concrete, or a breakage of the conglomerate.

Chloride etching is due to the ion chlorine, that is found, for example, in sea water. Chlorides cause a corrosive action on the reinforcing iron bars, which action removes the above-mentioned iron oxide passivating film and triggers a further rapid oxidation. Furthermore, sodium chloride may cause an alkali-aggregate reaction in the presence of amorphous silica, reaction which forms an alkaline silicate swelling in wet environments, and giving rise to devastating cracks. The salt, i.e., sodium chloride, is thus capable of damaging both the reinforcing iron bars, and the concrete containing reactive aggregates such as amorphous silicas. A similar degradation is caused by calcium chloride, which causes the corrosion of the reinforcing iron bars and which may further react with the calcium hydrate of the concrete, producing the calcium oxychloride hydrated, with a consequent devastating effect due to a volume increase.

The freeze-thaw cycles, due to the infiltration of water only, are a physical cause for degradation, due to the formation of ice, with a consequent volume increase (about 9%), which causes repeated pressures, that may cause cracks and crumblings in the concrete.

From what has been illustrated above, an urgent need is apparent, i.e., the need to accurately monitor both the presence of water, and humidity, and pH, and the state of corrosion of the reinforcing iron bars, by means of devices that, in turn, should be as much as possible not affected by the wear causes that are found inside the solid structure to be monitored.

In view of this, humidity sensors comprising an integrated circuit are known, based on the principle of the variation of a capacitance in a capacitor that is located outside of a passivating layer covering the integrated circuit.

However, if such known sensors were used to monitor building structures, the severe drawback of a considerable and rapid degradation of the sensor performance would occur, up to the complete unserviceability thereof, due to the corrosion of the metal electrodes of the capacitor, arranged outside of the passivating layer.

In addition, the above-mentioned known humidity sensors are not capable of detecting the parameter acidity/basicity, for example, in terms of pH, and they are not able to carry out direct and reliable assessments about the corrosion stage reached by the metal parts comprised in the structure to be monitored.

As regards the parameter acidity/basicity, pH sensors are known, i.e., detecting the concentration level of H+ ions in water, based for example on metal oxide electrodes, in which the potential difference created at such electrodes is measured, through different known possible methods: for example, in the case of the ISFET (Ion Sensitive Field Effect Transistor) there is a variation of the threshold voltage. Sensors of pH are also know, that are based on structures having an electrode that is inert with respect to the pH and an electrode that is made sensitive to the pH, by a pH sensitive layer (actually, these structures are capacitors having the pH sensitive layer as a dielectric, wherein the capacitance variations of such capacitors are measured as a function of pH).

Both types of known sensors are affected by the already mentioned drawback related to the rapid performance degradation due to the corrosion of the metal part of the sensor, when it is used inside a structure to be monitored.

Furthermore, even in this case, the known sensors to measure the pH are not capable of measuring humidity, nor of providing reliable information about the corrosion stage reached by metal parts comprised in the structure to be monitored.

Therefore, the above-mentioned prior art solutions leave unmet the need to provide sensors capable of detecting parameters of utmost importance, such as humidity and/or acidity and/or corrosion degree, preferably more than one, and which at the same time are sufficiently free from the mentioned degradation causes, so as to be suitable to be used in the widest operative conditions, for example, while being buried in building structures to be monitored.

SUMMARY OF THE INVENTION

Object of the present invention is to devise and provide an integrated electronic device, for detecting at least one parameter related to humidity and/or presence of water and/or acidity/basicity of an environment surrounding the device itself, so improved as to at least partially obviate the drawbacks described herein above with reference to the prior art and to meet the above-mentioned needs. In particular, object of the present invention is also to devise and provide an integrated electronic device for detecting at least a parameter related to any of the abovementioned phenomena (humidity and/or presence of water and/or acidity/basicity) of an environment surrounding the device.

Moreover, object of the present invention is also to devise and provide a monitoring system of such parameters and a method for detecting such parameters, which, by using the above-mentioned device, are in turn capable of meeting the above-mentioned needs.

An integrated electronic device includes first and second conductive members, and a measurement module including first and second measurement terminals respectively coupled to the first and the second conductive members. A separation layer may include an insulating material and may be configured to enclose the first and second conductive members and the measurement module so as to be separated from the surrounding environment. An electrode assembly may be on the separation layer and is exposed to the surrounding environment and adjacent the first and the second conductive members. The electrode assembly may form with the first and second conductive members an electromagnetic circuit having an impedance that varies based upon exposure to the surrounding environment. The measurement module may measure the impedance between the first and second measurement terminals to detect at least one parameter related to the humidity, presence of water, and acidity/basicity of the environment surrounding the device based on the measured impedance.

A monitoring system, may include an integrated electronic device as defined above, and includes an internal monitoring subsystem located within the solid structure and including a support structure passing through the points to be monitored inside the solid structure, and a plurality of devices carried by the support structure. Each device may further include an integrated antenna separate from the surrounding environment by the separation layer and operatively coupled with the measurement module the for wirelessly transmitting measurements and detections, a support on the separation layer and exposed to the surrounding environment, and an electromagnetic circuit carried by the support for wirelessly receiving the measurements and detections from the integrated antenna and for retransmitting the received measurements and detections representative of the at least one parameter to be monitored. An external control and data collection subsystem may be remotely located outside the solid structure and includes an external antenna communicating with the electromagnetic circuits of the plurality of detection devices for receiving the measurements and detections therefrom, and a processor to process the received measurements and detections.

A method for detecting at least one parameter related to humidity, presence of water, and acidity/basicity of an environment includes a) providing a device as defiend above, b) operating the device so that the measurement module measures a reference impedance between the first and second measurement terminals, c) positioning the device within the environment to be monitored, d) operating the device so that the measurement module measures an overall impedance between the first and second measurement terminals, and e) dtermining the at least one parameter related to humidity, presence of water, and acidity/basicity of the environment based on the measured overall impedance and the measured reference impedance.

BRIEF DESCRIPTION OF THE DRAWINGS

Further characteristics and advantages of the electronic detecting device, the detecting system and method according to the invention, will be apparent from the description set forth below of preferred implementation examples, given by way of indicative, non-limiting example, with reference to the appended figures, in which.

DETAILED DESCRIPTION

Figure 1:
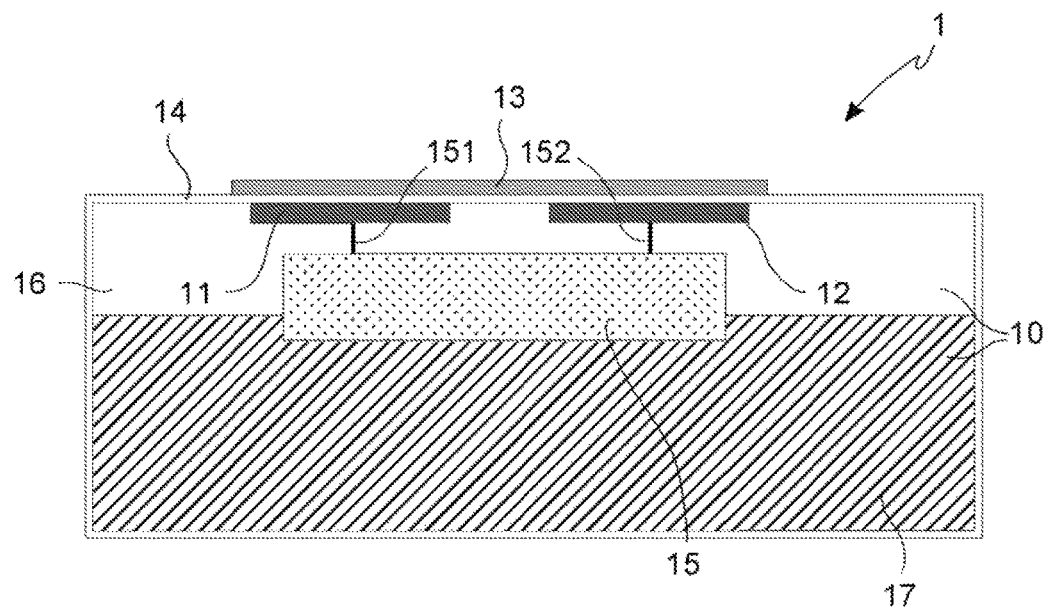
FIGS. 1 and 2 are side sectional views of a device according to two different embodiments comprised in the invention.

With reference to the FIGS. 1-13, an integrated electronic device 1 for detecting at least one parameter related to humidity and/or presence of water and/or acidity/basicity of an environment surrounding the device is now described. In particular, the electronic device 1 of the invention is suitable for detecting at least one parameter related to any of the following phenomena of an environment surrounding the device: humidity and/or presence of water and/or acidity/basicity. Such device 1 comprises a separation layer 14 from the surrounding environment, having at least one portion of insulating material 14, and further comprises a first conductive member 11 and a second conductive member 12, made of an electrically conductive material (for example, metallic), arranged inside the separation layer 14, with respect to the surrounding environment, and separated from the surrounding environment by the separation layer 14.

The device 1 also comprises a measurement module 15, having two measurement terminals 151, 152, electrically connected with the first 11 and the second 12 conductive members, respectively; the measurement module 15 is configured to provide an electric potential difference between the first 11 and the second 12 conductive members.

The device 1 further comprises electrode means 13, configured to act as an electrode, arranged outside of the separation layer 14, with respect to the first 11 and the second 12 conductive members; the electrode means 13 are arranged so as to form, with the first 11 and the second 12 conductive members, an electromagnetic circuit 71-73 having an electromagnetic circuit overall impedance that is variable based upon the exposure to environmental conditions with a variable level of humidity and/or acidity/basicity.

The measurement module 15 is configured to measure the electromagnetic circuit overall impedance, which is present between the measurement terminals 151, 152, and to determine the at least one parameter to be detected, based upon the overall impedance measured.

In different embodiments comprised in the invention, each of the above-mentioned parameters to be detected is a level of humidity (or moisture), or a level of acidity/basicity, or a pH level, or an indication of the presence of water, or a degree of corrosion of a metal structure that is present within the environment surrounding the device.

According to an embodiment, the device 1 is capable of determining any combination or even all the above-mentioned parameters.

In different possible applications of the device according to the invention, the environment surrounding the device may be an atmospheric environment surrounding the device or an environment formed by a solid in a building material surrounding the device. In accordance with an embodiment, the separation layer 14 is a passivation and galvanic insulation layer, completely composed of an insulating and passivating material, such as, for example, silicon oxide, or silicon nitride, or silicon carbide. According to a particular embodiment, the separation layer 14 is part of a passivating, impermeable, and protective layer, surrounding the integrated circuit (or chip) 10 that forms the device, together with the electrode means 13 (which are the only part of the device outside the passivating layer) so that the integrated circuit is completely hermetically sealed and galvanically insulated from the surrounding environment.

Figure 6:
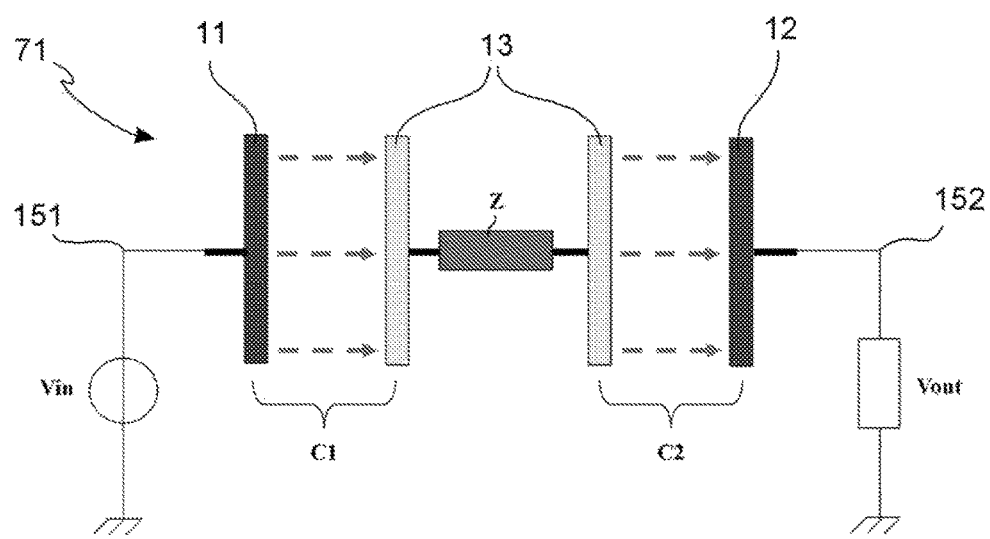
FIG. 6 shows a scheme of an electromagnetic circuit equivalent to the detecting device according to the embodiments illustrated in FIGS. 1 and 2.

With reference to the FIGS. 1 and 6, further details on an embodiment of the device 1 are now provided. First of all, it is noticed that, in the device 1 illustrated in FIG. 1, the electrode means 13 comprise a third conductive member 13, made of an electrically conductive material (for example, metallic), arranged so as to form with the first conductive member 11 a first capacitor C1, having a respective first capacitance C1, and with the second conductive member 12 a second capacitor C2 having a respective second capacitance C2. The third conductive member 13 connects the first capacitor C1 and the second capacitor C2 through a respective external impedance Z, so that the electromagnetic circuit 71 comprises the series of said first capacitor C1, external impedance Z, and second capacitor C2, and so that the overall impedance of the electromagnetic circuit comprises the series of said first capacitance C1, external impedance Z, and second capacitance C2.

Therefore, it can be observed that the electromagnetic circuit 71, schematized in FIG. 6, is the equivalent circuit of the device 1 represented in FIG. 1, and it illustrates the operation thereof. Furthermore, it is noticed that such electromagnetic circuit 71 partially extends inside the device 1, with respect to the separation layer 14, and partially outside it.

The measurement module 15 of the device 1 comprises an electric potential source Vin (indicated, with respect to the ground, in FIG. 6) and a circuitry capable of detecting the overall impedance of the electromagnetic circuit 71, for example by measuring the potential Vout (also indicated, with respect to the ground, in FIG. 6) as a function of Vin.

The measurement module 15 can be configured to generate an electric voltage that is constant or variable.

Since, as it will be illustrated herein below, the influence of the parameters to be detected particularly affects the imaginary part of the overall impedance, which therefore has to be suitably measured, the measurement module 15 is advantageously configured to generate a sinusoidal electric voltage at a preset frequency.

In an alternative embodiment of the measurement module 15, it is configured to generate signals with a variable frequency, according to controlled cycles, and to measure the overall impedance of the electromagnetic circuit through the detection of the resonance frequency of such circuit.

In accordance with an embodiment, the measurement module 15 comprises circuits, among which also an optional processor, configured to store initial calibration data, to carry out measurements relative to the parameters to be detected, to store the carried out measurements, and to estimate or assess the parameters to be detected based on the stored initial calibration data, on the carried out measurements and on the stored data relating to previous measurements. Further details on the dependence of the parameters to be detected and on the measurements and processing operations that are carried out to determine such parameters will be provided in the following of this description, when the detecting method according to the invention will be illustrated.

With reference again to the lateral sectional view set forth in FIG. 1, it shall be noticed that the measurement module 15, the first and second conductive members 11, 12 (and optionally further circuits) are integrated in a portion of functional circuitry 16 of the chip 10 of the integrated electronic device 1, obtained on a substrate 17, for example in silicon, of the same chip.

With reference to the first and the second conductive members, in the context of the embodiment of the device of FIG. 1, it shall be noticed that they may have different configurations. Some implementation examples, non-limiting with respect to further possible configurations, are described herein below.

According to an example, each of them is formed by one or more metallic plates having any shapes.

Figure 3A:
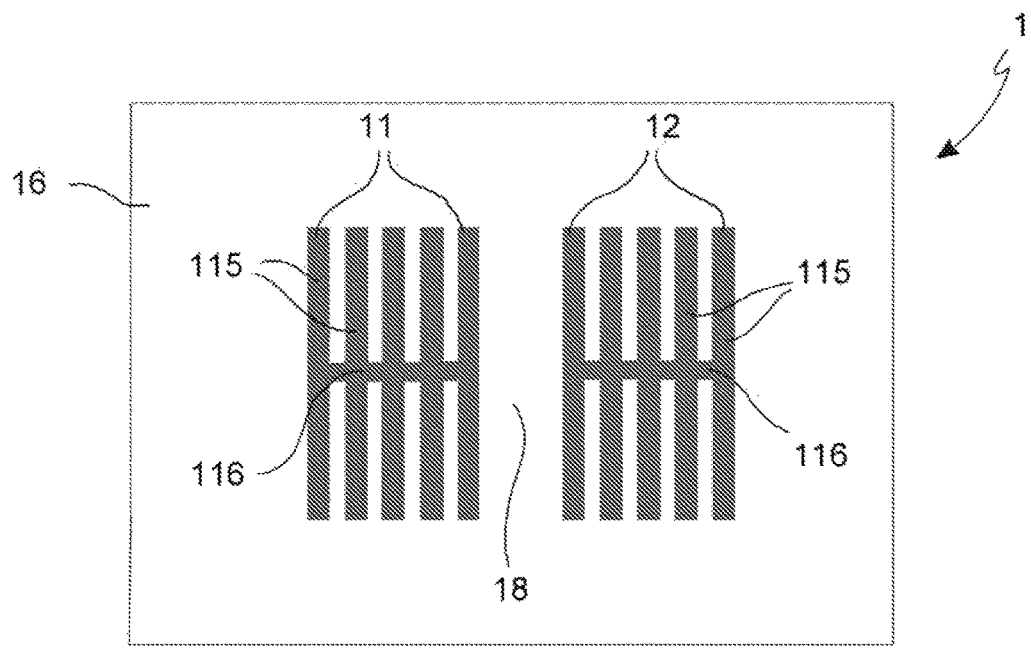
FIGS. 3A and 3B show two possible configurations, as seen from above and in a section beneath a passivating layer, of conductive members comprised in the device of the invention.

According to another example, illustrated in FIG. 3A, the first 11 and the second 12 conductive members have the same shape; each of them is formed by conductive segments (for example, metallic) arranged in the shape of a double comb. More particularly, each conductive member comprises a set of mutually parallel conductive segments 115, and a further conductive segment 116 transversal (for example, perpendicular) to the parallel segments, which connects them at a central position.

The interdigitated structure, described above, is advantageously adopted in the case when the device 1 comprises further functional members (for example antennae) that could determine undesired spurious currents on the conductive members. Such spurious currents are eliminated, or considerably reduced, by virtue of the interdigitated structure.

Figure 3B:
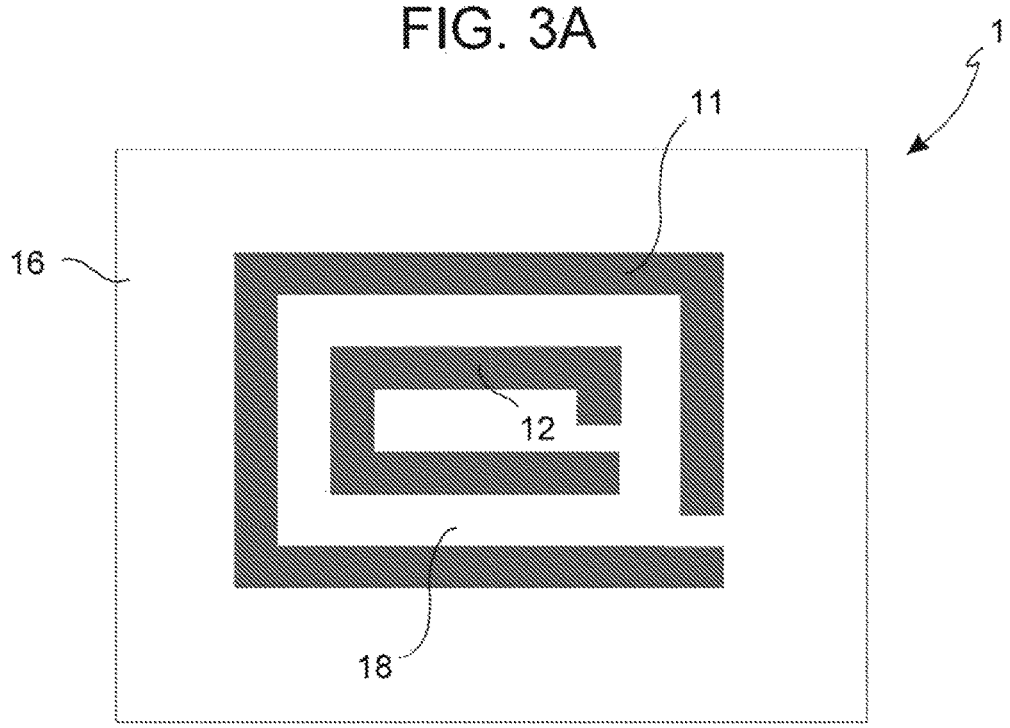

FIG. 3B illustrates a further possible configuration of the conductive members 11, 12, which provides two conductive stripes 11, 12 extending respectively along the perimeter of two similar polygons, one inside the other one; one of the two stripes corresponds to the first conductive member 11, the other one to the second conductive member 12.

It is noticed that, in all the embodiments illustrated above, it is provided that the first 11 and the second 12 conductive members are separated by an internal insulating material 18 and are arranged at such a distance as to not generate parasitic capacitances through such internal insulating material. Thus, advantageously, the electric field generated thereby, when an electric potential is applied thereto, is substantially normal with respect to each conductive member (i.e., to each capacitive armature), while, ideally there are no electric field lines between the armatures corresponding to the first and the second conductive members. As already noticed above, such electric field can be constant or variable in time; it is preferably variable.

It is noticed that both the first 11 and the second conductive members 12 are arranged inside the passivating layer 14, and thus they are protected against wear deriving from any external agent.

With reference to the third conductive member 13, in the context of the device embodiment of FIG. 1, it shall be noticed that it can have different configurations. Some implementation examples, not limiting with respect to further possible configurations, are described herein below.

The third conductive member 13 comprises at least one portion made of an electrically conductive material, arranged on the separation layer so as to form, for example, a geometric pattern comprising a plurality of stripe stretches (i.e., stripe lengths) and a plurality of interstitial spaces (i.e., interspaces) comprised between the stripe stretches; at least one first portion of the geometric pattern of the stripe is close to the first conductive member 11, overlapping it and spaced apart therefrom by the separation layer 14; at least one second portion of the geometric pattern of the stripe is close to the second conductive member 12, overlapping it and spaced apart therefrom by the separation layer 14. By virtue of such partial overlappings of the third conductive member 13 on the first and the second conductive members 11, 12, and taking into account the interposed separation layer 14, the already mentioned first capacitor C1 and second capacitor C2 are formed, which are part of the overall impedance to be measured. It is noticed that such capacitors comprise a first armature internal to the separation layer 14 and a second armature external thereto.

Figure 4A:
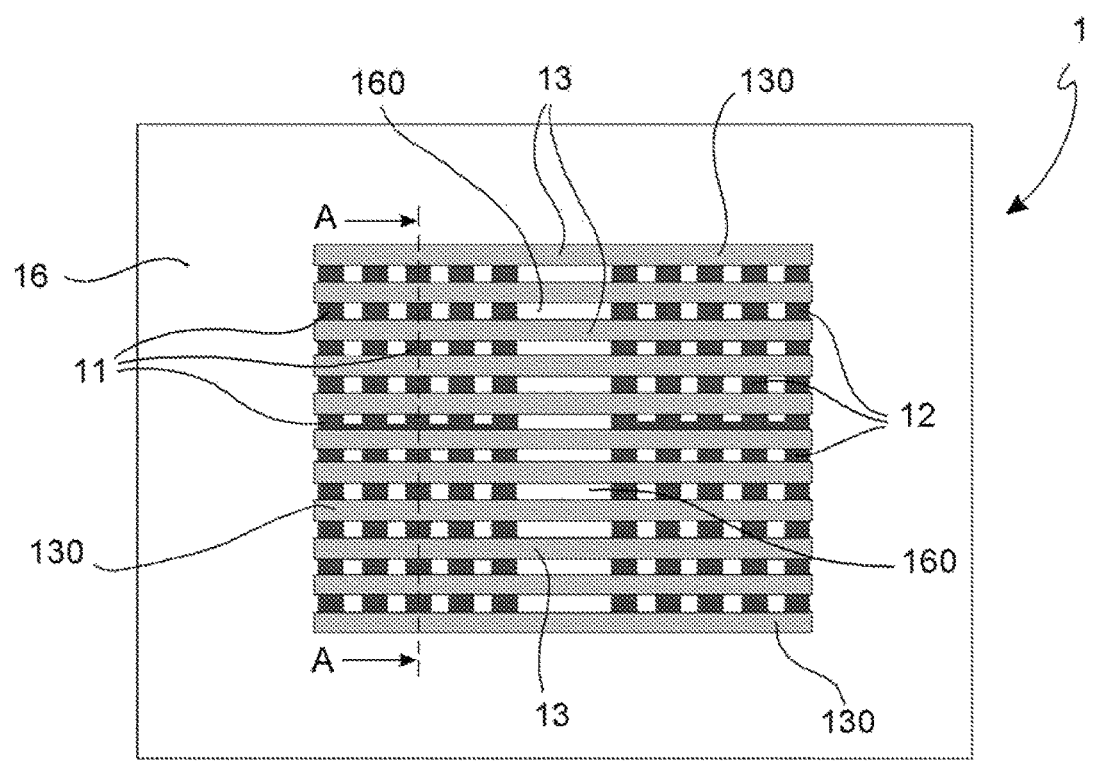
FIGS. 4A and 4B show two possible configurations, as seen from above, of electrode means comprised in the device, in the case when the conductive members have the configuration shown in FIG. 3A.

According to an implementation example, represented in FIG. 4A, the third conductive member 13 comprises a plurality of mutually substantially parallel conductive segments 130. Advantageously, such segments are mutually insulated, in such a way to nullify or reduce possible undesired spurious currents.

Figure 4B:
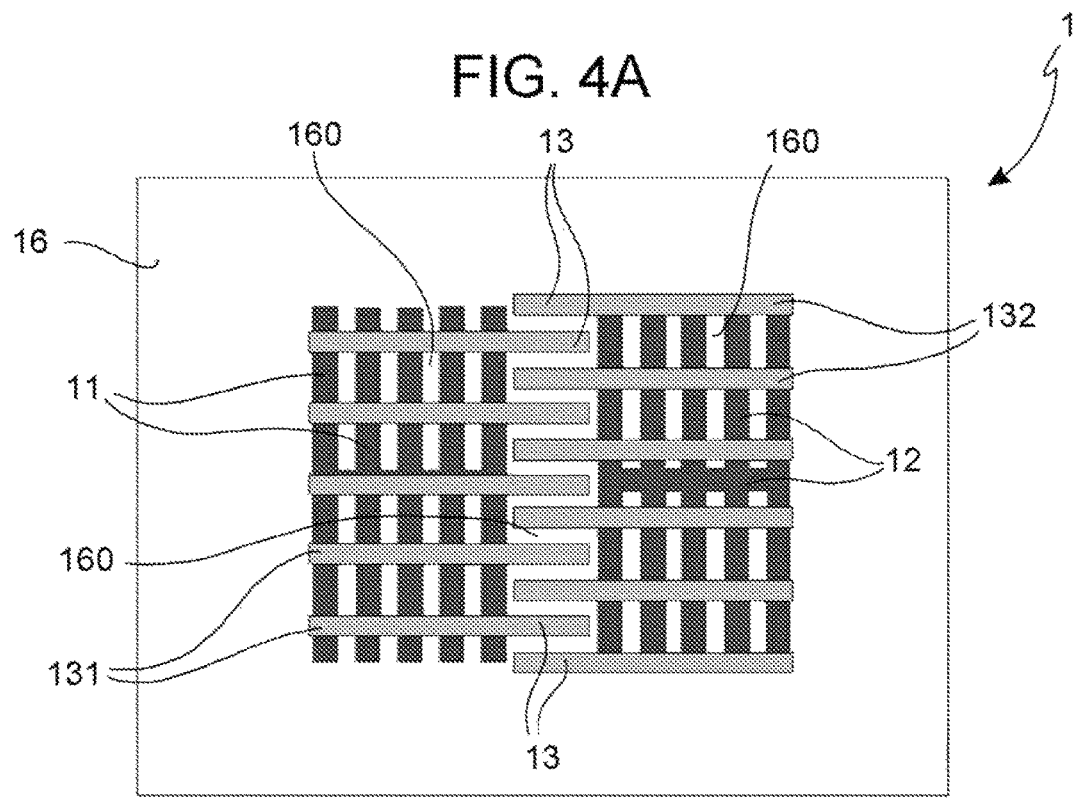

In another implementation example, represented in FIG. 4B, the third conductive member 13 comprises two sets of conductive stripes 131, 132, arranged in an interdigitated configuration, that is aimed to minimize spurious currents also in this case. One of the sets of stripes (indicated with 131) partially overlaps the first conductive member 11, the other set of stripes (indicated with 132) partially overlaps the second conductive member 12. The two sets of stripes 131 and 132 form a further interdigitated capacitor in a region extending between said portions overlapping the first and the second conductive members 11 and 12.

It is noticed that, in FIGS. 4A and 4B, the mutual positioning between the first and second conductive members 11, 12 is illustrated, beneath the separation layer 14, and the third conductive member 13, above the separation layer 14. For illustrative purposes, it is supposed that such conductive layer 14 is transparent, so that the first and the second conductive members are visible. Therefore, the separation layer 14 is not visible in the FIGS. 4A and 4B but it shall be remembered that it is present.

In the FIGS. 4A and 4B, the interstitial spaces are indicated with the numerical reference 160.

Figure 5A:
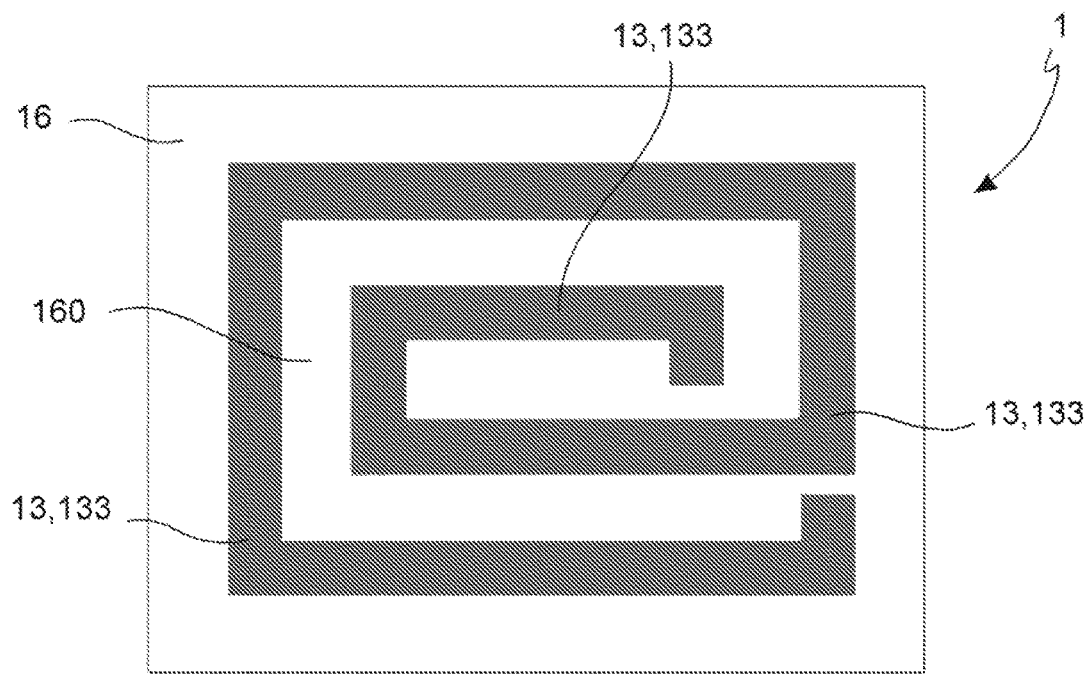
FIGS. 5A and 5B show two further possible configurations, as seen from above, of electrode means comprised in the device, according to two respective further implementation examples.

In accordance with a further implementation example, the third conductive member 13 comprises a conductive stripe extending along an open or closed polygonal line formed by segments that are parallel two by two. Particularly, as shown in FIG. 5A, the conductive stripe 133 extends along a line describing a spiral overlapping the first and the second conductive members 11 and 12 of FIG. 3B.

Figure 5B:
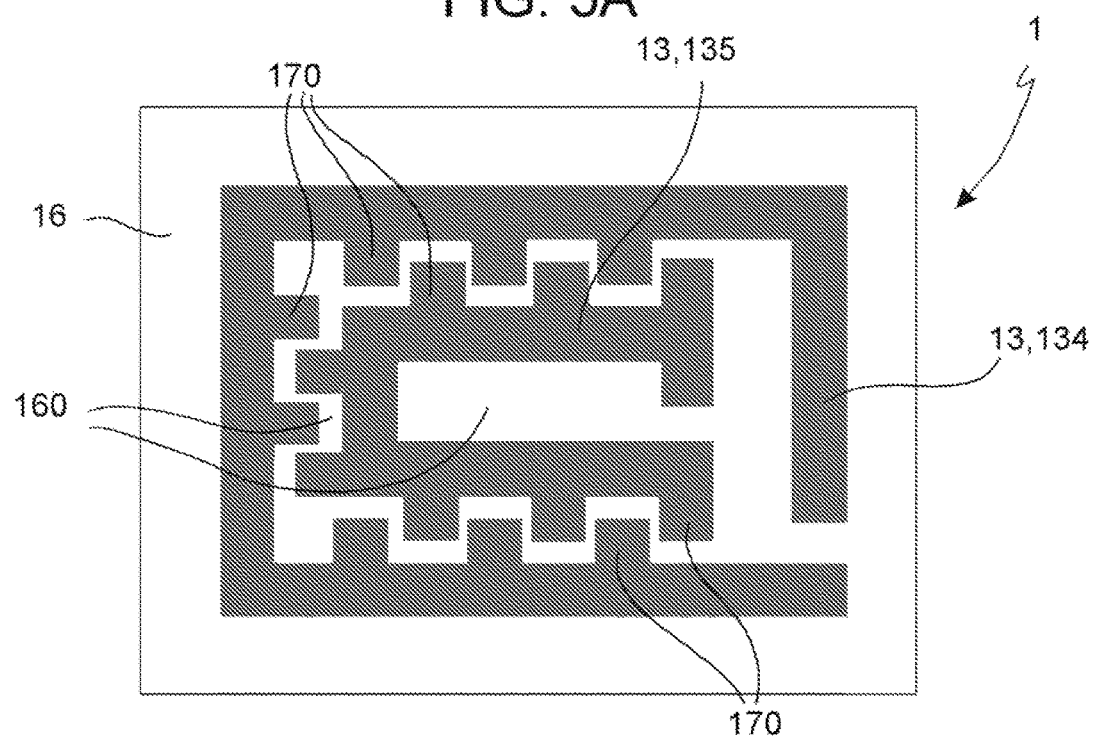

According to a further implementation variant, shown in FIG. 5B, the third conductive member 13 comprises two conductive stripes 134, 135 extending respectively along the perimeter of two similar polygons, one inside the other one; further interdigitated structures 170 can be present between the two conductive stripes 134, 135.

It is noticed that the device, according to the embodiment and the variants described before, is suitable to operate while being buried in a structure of a solid material to be monitored, and it is configured to detect a level of humidity and/or acidity/basicity of such solid material, and to further detect a corrosion degree of metal structures contained inside the solid material to be monitored.

According to a significant, non-limiting application example, the structure to be monitored is in reinforced concrete, the solid material to be monitored is concrete, and the metal structures to be monitored are metal rods, or reinforcing iron bars, of the reinforced concrete.

In this type of application, the above-mentioned interstitial spaces 160 of the third conductive member 13 are arranged so as to be filled by the solid material to be monitored, after the device 1 has been buried and it is in operative conditions.

In such a case, the overall impedance of the electromagnetic circuit depends on the humidity level and/or the presence of water and/or the acidity/basicity level of the solid material or the absorbing material contained in the interstitial spaces 160 of the third conductive member 13. The details of such dependences will be illustrated in the description of the detecting method according to the invention.

Figure 7:
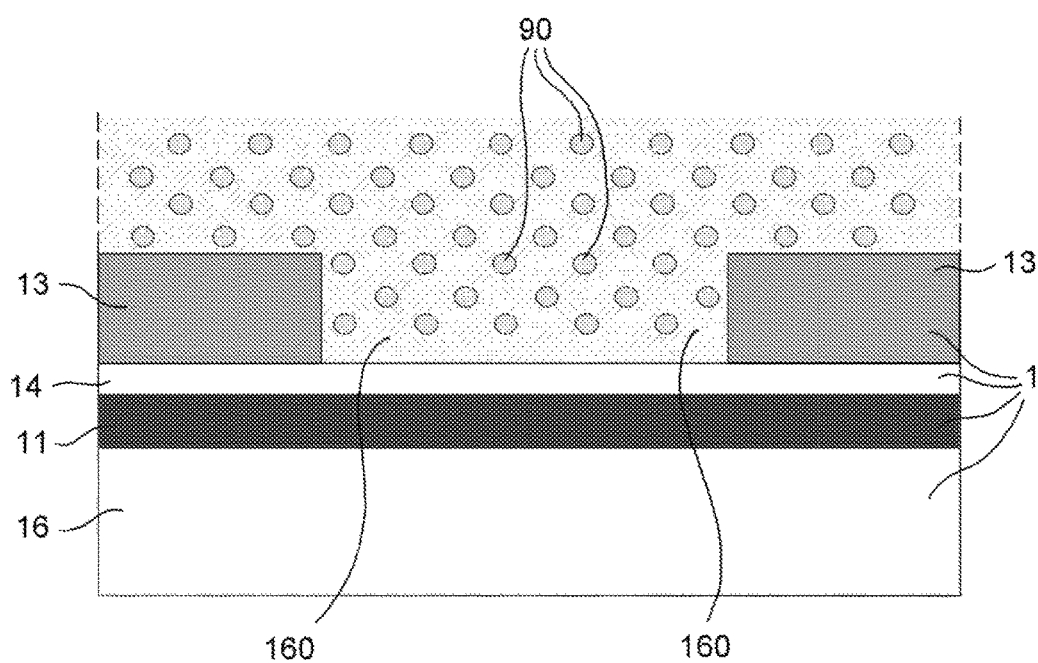
FIG. 7 illustrates a view along a partial portion of the lateral section A-A of the device of FIG. 4A, in the presence of concrete soaked with drops of water/humidity.

In FIG. 7, the presence of drops 90 of water or humidity, inside the interstitial spaces 160 between the stripes 130 of the third conductive member 13, is illustrated. The presence of water and extraneous chemical substances, in the building material, may reduce or, more generally, may change the pH, determining those degradation phenomena already illustrated in the description of the technological background, for example, by generating corrosion phenomena on the conductive stripes (for example, metallic stripes).

Figure 8:
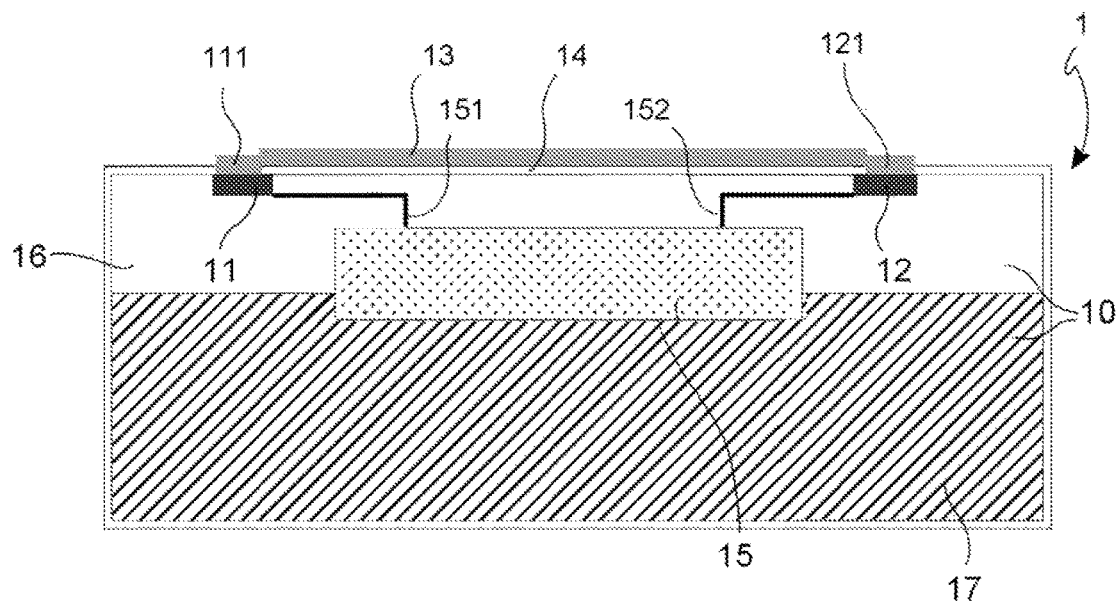
FIG. 8 is a lateral sectional view of a further embodiment of the device according to the invention.
Figure 9:
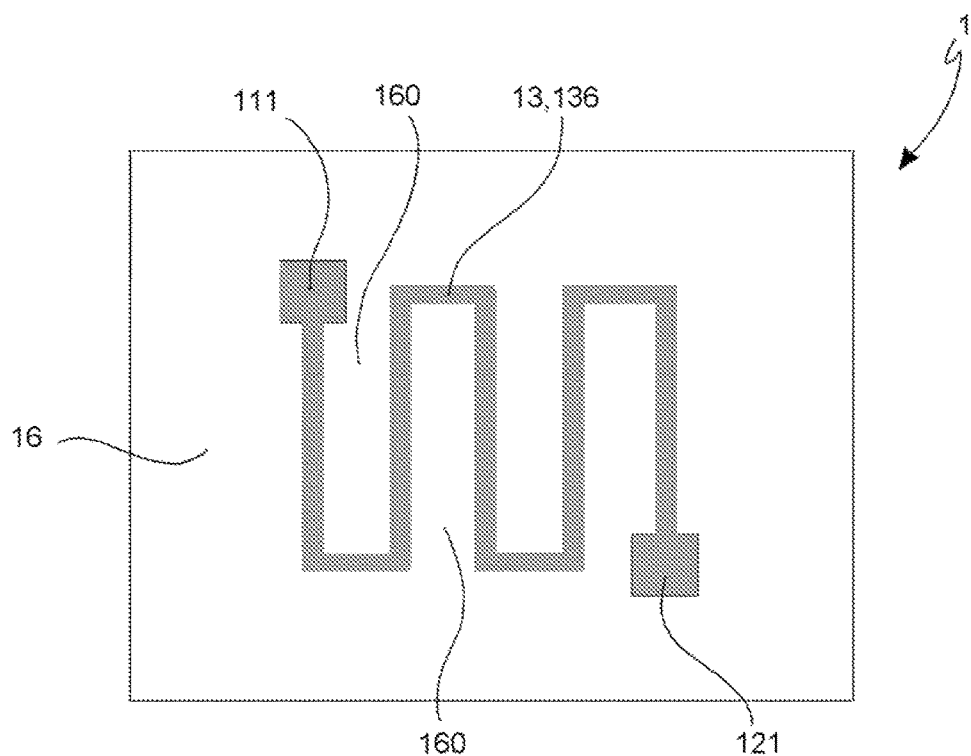
FIG. 9 illustrates a configuration, as seen from above, of electrode means comprised in the device of FIG. 8.
Figure 10:
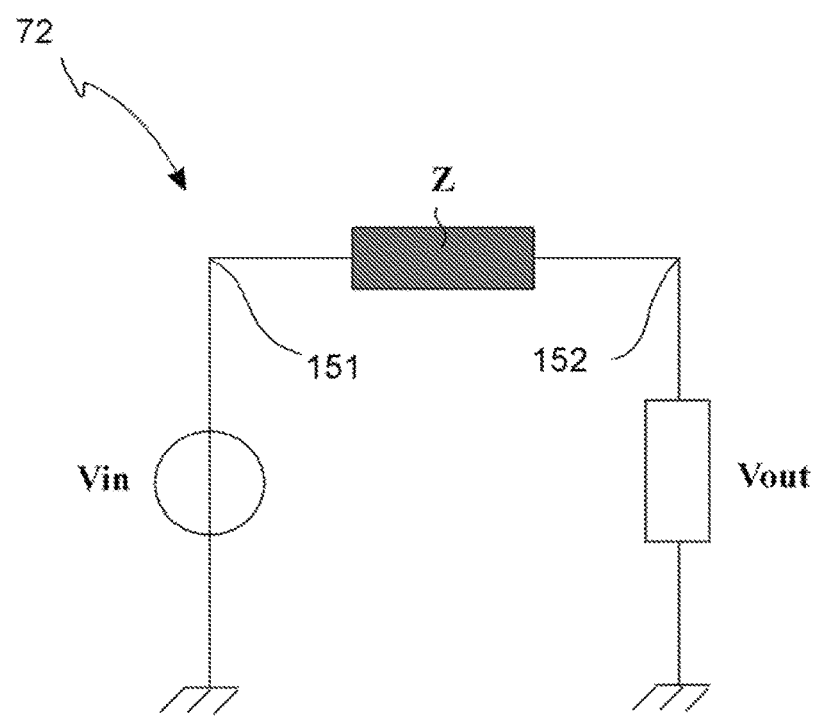
FIG. 10 shows a scheme of an electromagnetic circuit equivalent to the detecting device of FIG. 8.

With reference now to the FIGS. 8-10, a further embodiment of the device 1, according to the invention, is described. Such embodiment corresponds to the one hereto illustrated (and the different variants), except in that the first 11 and the second 12 conductive members comprise connecting metal pads 111, 121, opening in the separation layer 14, in contact with the third conductive member 13. Therefore, in such a case, the overall impedance of the electromagnetic circuit (schematized in the equivalent circuit 72 of FIG. 10) comprises the external impedance of such third conductive member 13, and it does not comprise the first and the second capacitors, illustrated in the previous embodiment.

According to an implementation variant, illustrated in FIG. 9, the third conductive member 13 comprises a conductive stripe 136 (for example, a metallic stripe) extending through segments forming a continuous open polygonal line, connecting the two pads 111, 121. The segments are shown as parallel two by two, but of course, other configurations are possible.

The external impedance Z of the third conductive member 136 comprises in this case a resistive part, due to the continuous conductive stripe 136, and a capacitive part, due to capacitive effects that are created between the mutually parallel segments of the stripe, through the material deposited in the interstitial spaces 160.

In all the device embodiments hereto mentioned, the conductive stripes 130-136 forming the third conductive member 13 can be, in an implementation example, metallic stripes obtained by ink-jet moulding onto the passivating layer 14.

Such metal stripes are preferably made of the same metal composing the internal metal structures of the structure to be monitored (for example, iron, steel, or other), which therefore undergoes a similar corrosion, with a good approximation.

Figure 11:
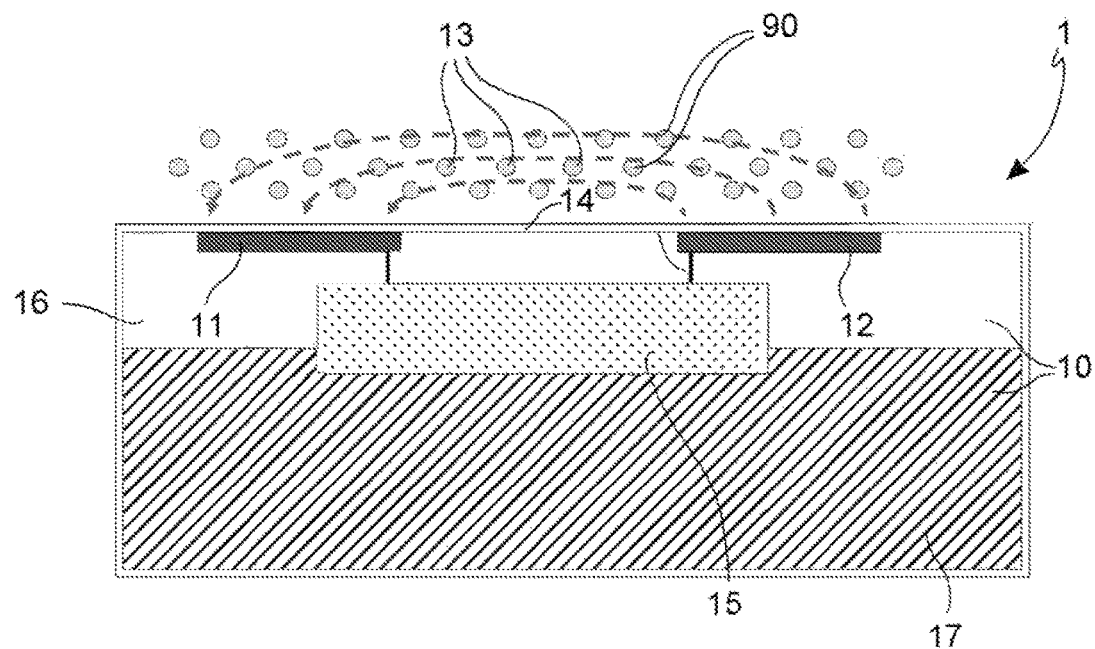
FIG. 11 is a lateral sectional view of a further embodiment of the device of the invention.
Figure 12:
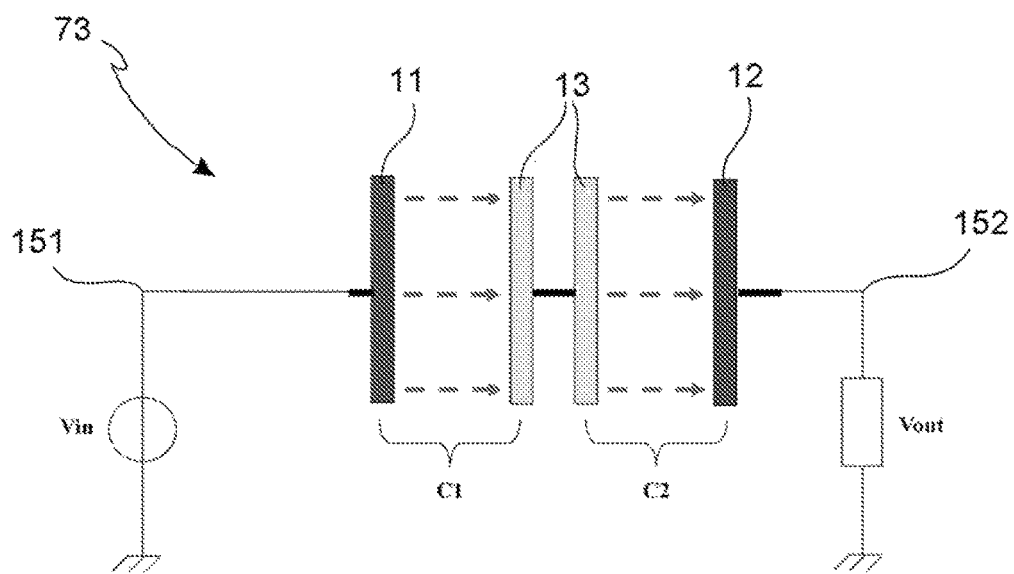
FIG. 12 shows a scheme of an electromagnetic circuit equivalent to the detecting device of FIG. 11.

With reference now to the FIGS. 11 and 12, a further embodiment of the device 1 according to the invention is described. Such embodiment corresponds to those hereto illustrated (including the different variants thereof), except for the following aspects: the electrode means 13 comprise equivalent electrode means 13 formed by water and/or humidity (for example, the drops 90) that is present in contact with or in the proximity of the separation layer 14, so as to form with the first conductive member 11 a first equivalent capacitor C1, having a respective first equivalent capacitance C1, and with the second conductive member 12 a second equivalent capacitor C2, having a respective second equivalent capacitance C2. Such equivalent electrode means act as an equivalent external impedance, having a respective value of equivalent external impedance. Therefore, the electromagnetic circuit 73 comprises in this case the series formed by first equivalent capacitor C1, equivalent external impedance Z, and second equivalent capacitor C2; the overall impedance of the electromagnetic circuit 73 comprises the series of first equivalent capacitance C1, equivalent external impedance Z, and second equivalent capacitance C2.

It is noticed that the embodiment described in FIG. 11 may correspond to a state of use of a device according to the other embodiments, once the corrosion of the third conductive member (placed outside of the passivating layer 14) is completed, or has exceeded a preset degree. So, also in such case, the device 1 maintains a useful functionality, providing the following information: the occurrence of a very advanced corrosion of the external metal element, and therefore, presumably, of the metal structures inside the building structure; the optional presence of water and the pH of such water.

This is observed in the moment when the equivalent impedance measured by the measurement module 15 decreases from a very high value, basically infinity (which is found when water is absent and the third conductive member, severely corroded, is in non-operative conditions), to very low values, caused by the presence of water, accumulated in the proximity of the passivating layer 14, which water, due to its own conductive properties, deviates the lines of force of the electric field and causes in fact a connection between the zones overlapping the first and the second conductive members 11 and 12, forming therewith respective equivalent capacitors.

More particularly, the particles of water 90, by electric induction, change the lines of force of the electric field and constitute an equivalent external armature. Therefore, it is possible to measure the presence of water by virtue of the variation of capacitance of such equivalent capacitor. Similarly, in the case of a presence of acid or basic ions near to the equivalent armatures, which ions alter the electric charge of the equivalent capacitor, the same principle is used to measure the pH variation.

As in the other embodiments, the measurement module 15 is configured to apply an electric voltage that is continuous or, preferably, variable.

If the signal Vin is variable in time, the variation of the peak value or peak-to-peak value or effective value (e.g., r.m.s.) of the output signal Vout can be measured, for example, to evaluate the capacitance variation of the equivalent impedance. Alternatively, if Vin is variable, e.g., sinusoidal, the device 1 can advantageously comprise a resonant circuit LC in series or parallel (introducing an inductance, not shown in Figures) so as to measure the variation of a parameter of such circuit, such as for example the resonance frequency, to be able to evaluate the pH variation. In fact, the presence of ions due to pH alters the charge of the equivalent capacitor, and therefore the capacitance thereof.

Figure 2:
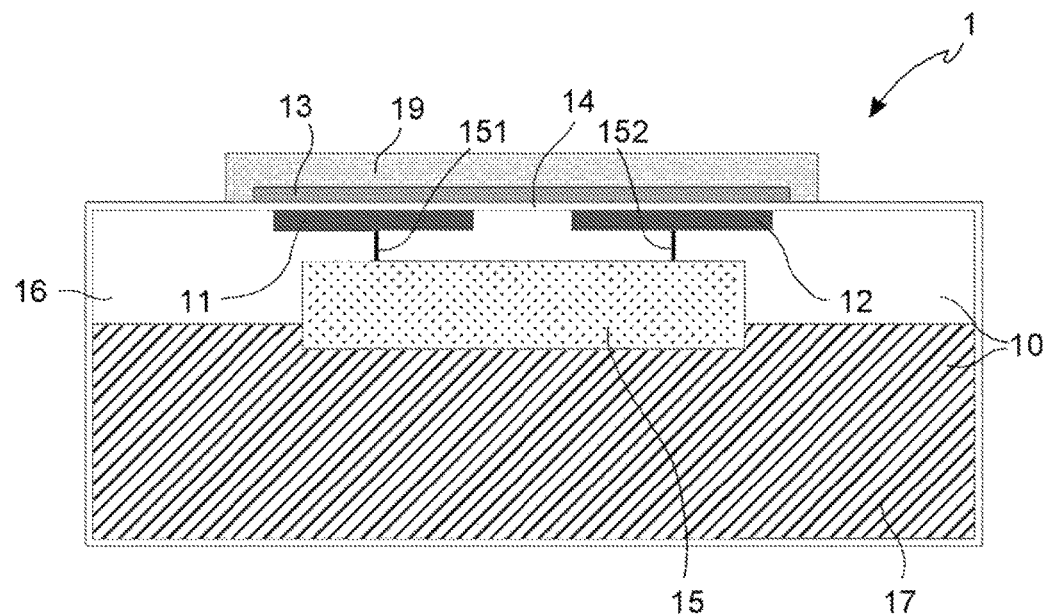

With reference now to the FIG. 2, another embodiment of the device 1 according to the invention is described. Such embodiment corresponds to the one shown in FIG. 1 (and the different variants), except in that it further comprises a portion of absorbing material 19, for example dielectric and/or polymeric, suitable to absorb humidity and/or water from the surrounding atmospheric environment, in a manner that is indicative of the humidity and of the acidity/basicity of the atmospheric environment.

The absorbing material 19 is arranged so as to fill the interstitial spaces of the third conductive member 13, and it covers the third conductive member 13, while at least partially containing it. According to an implementation example, not depicted, the absorbing material 19 is arranged in contact with the separation layer 14 and completely surrounds the third conductive member 13, so as to form a further inter-electrode layer, in addition to the passivating separation layer 14.

In the embodiment of FIG. 2, the overall impedance of the equivalent electromagnetic circuit depends on the humidity level and/or the presence of water and/or the acidity/basicity level of the absorbing material 19 contained in the interstitial spaces of the third conductive member 13.

In such embodiment, the device 1 is suitable to operate in an external environment, and the surrounding environment to be monitored is an atmospheric environment. In such a case, it is also possible to replace the absorbing material 19 and the third conductive member 13, since they are separated, by the separation layer 14, from the first 11 and the second conductive member 12.

Figure 13:
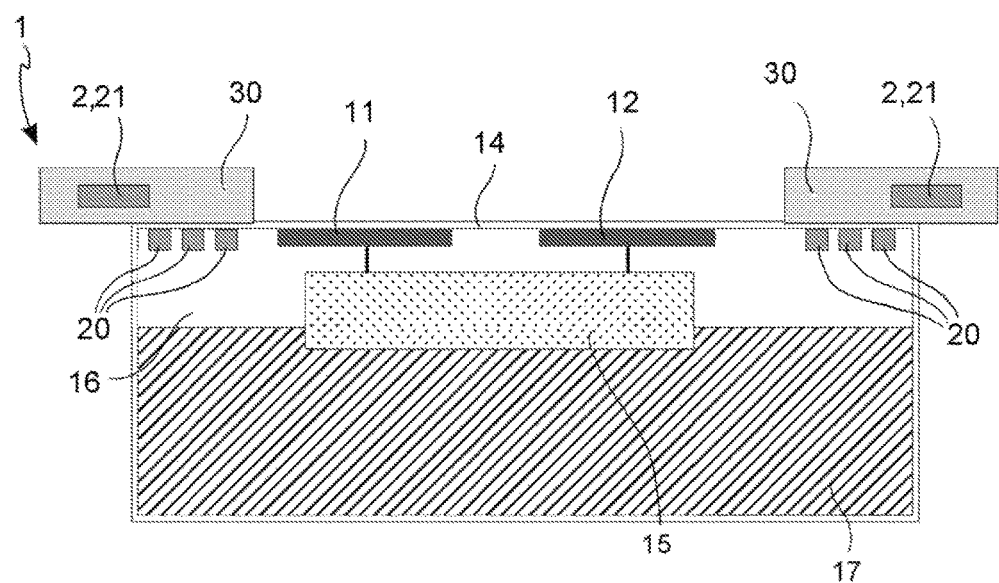
FIG. 13 is a lateral sectional view of a further embodiment of the device according to the invention.

In accordance with a further embodiment, illustrated in FIG. 13, the device 1 further comprises an integrated antenna 20, operatively connected, within the functional circuitry 16, with the measurement module 15, to receive data relating to measurements and detections that are carried out, and to transmit them in wireless mode. Furthermore, the device 1 comprises electromagnetic means 2 for electromagnetic expansion/concentration, connected in wireless mode to the integrated antenna 20, to receive the data transmitted thereby and to retransmit them in wireless mode.

Finally, the device comprises a support 30, for example in polymeric material, on which the detecting device 1 and the electromagnetic means 2 are positioned (for example, glued) and kept mutually integral.

The detecting device 1 of FIG. 13 comprises structures that are similar to those shown in FIG. 11 to measure humidity and acidity/basicity of the surrounding atmospheric environment.

However, hybrid embodiments are possible, where such structures are similar to what has been shown in FIG. 1 or 2 or 8, and in such cases, the support 30 can comprise the third conductive member 13 in a manner similar to what has been shown in FIG. 2 with reference to the absorbing material 19.

The integrated antenna 20 has the function of transmitting outside of the detecting device 1, in a wireless mode, the measured data, i.e., the intensity of each of the electric variables depending on and representative of, respectively, one of the parameters to be detected. The integrated antenna 20 can further have the function of receiving operative commands from the outside. Moreover, the integrated antenna 20 can have the further function of receiving radiofrequency waves that may be necessary for a remote power supply of the detecting device 1, without needing batteries or power supplies in loco.

The electromagnetic means 2 meet the need to allow a communication between the device 1 and an external control and data collection system, located remotely, for example, at distances of some centimeters or meters from the structure to be monitored, and thus from the device 1. To this aim, the electromagnetic means 2 perform a function of expansion and electromagnetic concentration. The electromagnetic means 2 comprise at least two mutually connected antennae, a first antenna 21 and a second antenna 22.

Figure 14:
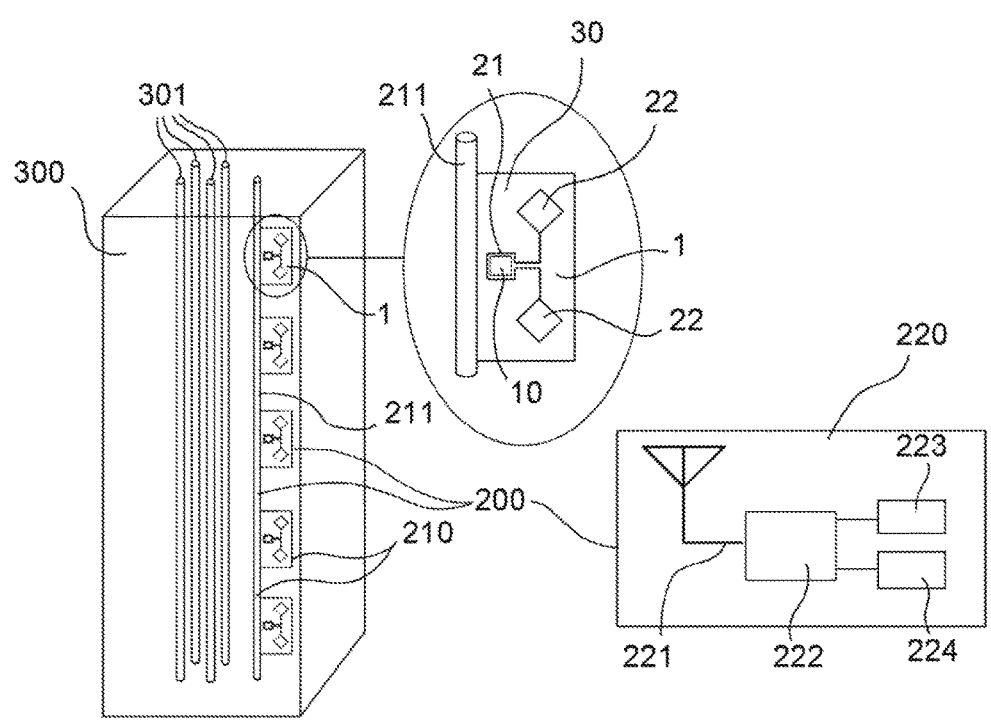
FIG. 14 is a diagram of a detecting system, comprising a plurality of monitoring devices according to the invention.

In the lateral sectional view of FIG. 13, the integrated antenna 20 and the first antenna 21 of the electromagnetic means 2 are visible. In the detail of FIG. 14, which shows a possible physical structure of the device 1, the second antenna 22 is visible too.

The first antenna 21 communicates with the integrated antenna 20 preferably through a magnetic field coupling. The second antenna 22 communicates with a remote antenna, for example of the external data control and collection system, through far-field electromagnetic coupling.

The electromagnetic means 2 and the integrated antenna 20 are per se known. Further details about the manner in which they can be manufactured can be found, for example, in the international patent application WO 2012/084295, by the Applicant.

With reference to FIG. 14, a monitoring system 200 of at least one parameter related to humidity and/or presence of water and/or acidity/basicity, in a plurality of points inside a solid structure 300, is now described. Such system 200 comprises an internal monitoring subsystem 210 located within the solid structure 300; and an external control and data collection subsystem 220 located outside and remotely with respect to the solid structure 300.

The internal monitoring subsystem 210 comprises a support structure 211 passing through the points to be monitored inside the solid structure 300, and further comprises a plurality of detecting devices 1, according to the embodiment in which each of them comprises an integrated antenna and electromagnetic concentration/expansion means. Each of the plurality of detecting devices 1 is secured to the support structure 211 in a known and predetermined position by the respective support 30.

The external control and data collection subsystem 220 comprises an external antenna 221, capable of electromagnetically communicating with the electromagnetic means 2 of the detecting devices 1; and further comprises data collection, storage, and processing means 222, suitable to receive, store, and process data coming from a plurality of detecting devices 1 representative of parameters to be monitored; such means 222 comprise a processor configured to store initial calibration data, to operate measurements relative to the parameters to be detected, to store the carried out measurements, and to estimate or assess the parameters to be detected based on the stored initial calibration data, the carried out measurements and the stored data relating to previous measurements.

In the example of FIG. 14, the structure to be monitored is a pillar in reinforced concrete 300, comprising reinforcing steel bars 301, which can be used as a support structure 211.

Further details about the manner in which a monitoring system 200, having the characteristics indicated above, can be obtained, can be found in the international patent application WO 2012/084295, by the Applicant.

In a further embodiment (not depicted), the external antenna 221 and the second antenna 22 can be omitted, and at least one detecting device 1 can be connected via a cable to the external data control and collection unit 220.

Figure 15:
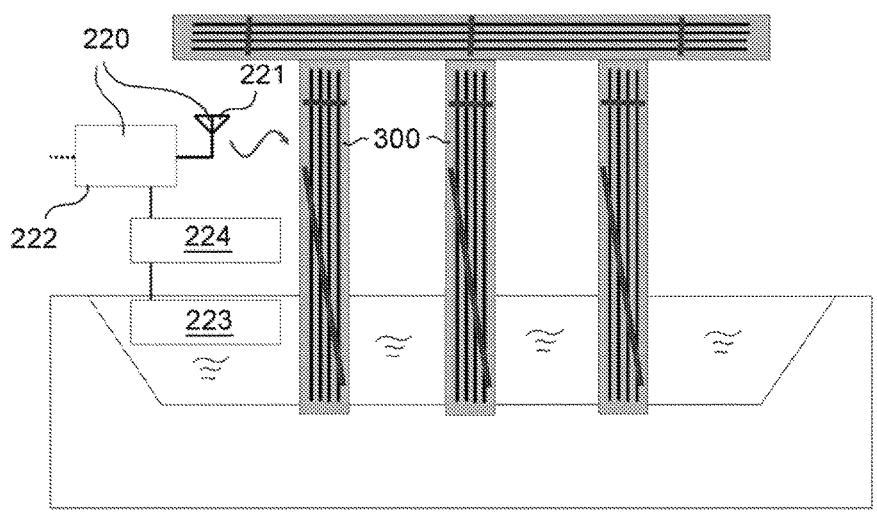
FIG. 15 illustrates an application example of the system of FIG. 14.

FIG. 15 illustrates a particular embodiment of the system 200, and a particular application scope. The structure to be monitored 300 comprises a plurality of support pillars 301 for a bridge, in reinforced concrete, partially immersed in a water course or basin. The monitoring system 200, in addition to the characteristics described before, also comprises in this case further sensors 223, 224 of external humidity and/or pH, connected to the processor of the external subsystem 220 to communicate data relating to the measured parameters; this allows the processor to perform a more refined processing operation, which takes into account the data measured by such further external sensors.

For example, the external sensor 223 is a pH sensor located within the water in which the pillars 300 are partially immersed: this can provide important auxiliary information to be related to the pH measurements carried out by the sensors inside the pillars. Similarly, the further external sensor 224 is a humidity sensor located in an atmospheric environment adjacent to that in which the pillars are: this can provide important auxiliary information to be related to the humidity measurements carried out by the sensors inside the pillars.

Herein below, a method for detecting at least one parameter related to humidity and/or presence of water and/or acidity/basicity of an environment will be described, which method is implemented by means of detecting devices as those described above.

According to an embodiment, such method comprises the following steps:

a) providing an integrated electronic detecting device 1 comprising: a separation layer 14 from a surrounding environment, formed at least partially by an insulating and/or passivating material; a first conductive member 11 and a second conductive member 12, made of an electrically conductive material, arranged inside the separation layer 14, with respect to the surrounding environment, and separated from the surrounding environment by the separation layer 14; a measurement module 15, having two measurement terminals 151, 152, electrically connected with the first 11 and the second 12 conductive members;

b) measuring a reference impedance between said measurement terminals 151, 152;

c) arranging the device 1 within the environment to be monitored;

d) providing, by the measurement module 15, an electric potential difference between the first 11 and the second 12 conductive members;

e) measuring, by the measurement module 15, an overall impedance, which is present between the measurement terminals, referred to an equivalent electromagnetic circuit, extending at least partially outside of the separation layer 14, with respect to the first 11 and the second 12 conductive members;

f) determining the above-mentioned at least one parameter, based on the measured overall impedance and the measured reference impedance.

In accordance with a particular embodiment, the method also comprises the step of further providing, in the device 1, electrode means 13, configured to act as an electrode, arranged outside of the separation layer 14, with respect to the first 11 and the second 12 conductive members, wherein the electrode means 13 are arranged so as to form, with the first 11 and the second 12 conductive members, an equivalent electromagnetic circuit, having an overall impedance variable based upon the exposure to environmental conditions with a variable level of humidity and/or acidity/basicity.

It is noticed that the reference impedance can be measured in laboratory or in a buried condition. The reference impedance provides a base value for the device, and for example it is measured in conditions similar to the operative ones, i.e., when a building material similar to that to be monitored is comprised between the interstitial spaces of the third conductive member. Typically, such impedance is measured in conditions of absence of water, in the presence of a known value (for example, very low) of humidity, and for a reference pH value (typically, pH=14, such as the one that is expected within concrete pillars in initial conditions).

According to a particular embodiment, the method comprises the further step of arranging the first 11 and second 12 conductive members so that they are separated by an internal insulating material, and arranged at such a distance as to not generate parasitic capacitances, or anyhow to significantly reduce the effect thereof, through the internal insulating material, so that the of the reference impedance has a substantially infinite resistance.

In accordance with an embodiment of the method, it uses a detecting device 1, according to any of the embodiments of device described before, which is capable of detecting both a level of humidity, and the presence of water, and a pH value of such water, and the occurrence of a state of corrosion of a metal that is present in the environment to be monitored. In such a case, the step f) of the method comprises the following steps: determining a humidity level based on a variation of the value of the capacitive part of the overall impedance with respect to an initial calibration value referred to a known humidity level; determining a presence or absence of water based on the occurrence or not of a relative minimum/maximum peak of the overall impedance; if the presence of water is detected, determining a pH value of the water being present based on a comparison of the measured value of the relative minimum/maximum peak of the overall impedance with the initial calibration value, referred to a known pH level, and/or with relative minimum/maximum values measured at peaks previously detected; determining the occurrence of a state of advanced or complete corrosion of a metal that is present in the environment to be monitored when the value of the measured overall impedance, in the absence of water, exceeds a preset threshold; if a state of advanced or complete corrosion has been determined, determining the presence of water in the instants in which the measured overall impedance does not exceed said preset threshold, and reaches a relative minimum/maximum peak.

For each type of measurement, it is necessary to qualitatively understand the phenomena and the dependences on which the measurement is based. On the other hand, it is not necessary to express such dependences in an analytical form, since it is possible, from an operative point of view, to proceed to an initial characterization of the device, by means of the experimental determination of the curves that correlate the measured overall impedance to the related variation of each of the parameters to be determined. Such a characterization, also referred to as an initial calibration, leads to characterization data that are stored in the processor of the device and/or in the processor of the external subsystem of the monitoring system.

While taking into account the above reported notes, the qualitative phenomena, on which measurements are based, are synthesized herein below.

The level of humidity is estimated by observing the variations of the overall impedance measured; in fact, the imaginary part, particularly the capacitive part of such overall impedance, depends on the humidity of the material that is present in the interstitial spaces of the external electrode means, which affects the value of the capacitances that are present between the electrode means and, respectively, the first and the second conductive members; and further affects the capacitive part of the external impedance. Basically, as the humidity level increases, also the capacitive part of the overall impedance increases, and therefore the value of such overall impedance decreases. Typically, the humidity variations are reflected by gradual and "slow" variations of a "baseline" of the time trend of the overall impedance.

The presence of water is detected when observing rapid decrements of the measured overall impedance, leading to peaks of relative minimum. In fact, conceptually, the presence of a thin layer or a significant amount of water in the interstitial spaces of the electrode means causes a considerable increase of the capacitances involved, and it may further decrease (by virtue of the conductive properties of water) the real, i.e., resistive, part of the external impedance.

The value of the relative minimum peaks of the impedance, that may be observed, is related to the pH level, thus allowing an assessment thereof, once a reference peak value is known, corresponding for example to a pH value of =14. Therefore, it is possible to assess or evaluate relative pH values, with respect to the reference value, which is efficient and sufficient for the applications considered herein.

However, it is possible that also relative maximum peaks of the impedance may be related to the humidity level, the presence of water, the pH value. In fact, it is possible that the measurement module 15 can carry out the impedance measurements at a plurality of different frequencies, or generally in a band of frequencies, so that the overall behaviour of impedance can be obtained in such band, where the impedance can have maximum or minimum peaks. In other cases, different chemical substances can be present, which may give rise to a various behaviours of the measured impedance.

In alternative embodiments of the method, it is possible, instead of observing peak values, to use suitable data processing algorithms to obtain the parameters of interest or a variation thereof with respect to a reference value.

Finally, a state of advanced or complete corrosion of the metal forming the electrode means of the device is determined when the overall impedance value becomes particularly high, exceeding a threshold predefined in the initial calibration step. In fact, the corrosion causes interruptions in the metal paths of the electrode means, with an consequent increase (up to the infinity) of the resistance of the external impedance.

In the method according to the invention, the metal material of the electrode means of a device intended for a given structure (for example, reinforced concrete) is selected so as to be the same or very similar to that of the metal parts (for example, reinforcing irons) that are present in the structure. Consequently, the determination of a corrosion state of the electrode means provides a very reliable information about the state of corrosion, which is almost the same, experienced by the metal parts of the structure, surrounded by the same material in the same structure and exposed to conditions similar to those of the electrode means of the device.

It can be noticed that the object of the present invention is achieved by the detecting device (as well as by the monitoring system and the monitoring method according to the invention), by virtue of its own characteristics.

In fact, the detecting device of the present invention allows detecting one or more parameters relating to humidity and/or presence of water and/or acidity/basicity of an environment surrounding the device. Even a single device of the invention may allow determining both a humidity level, and a pH level, and the presence of water, and a degree of corrosion, as illustrated above. At the same time, the device of the invention is sufficiently robust, with respect to different causes of performance degradations, so as to be suitable to be used in the most different operative conditions, also while being buried inside a solid structure to be monitored.

Such an object is achieved by virtue of the functional and structural aspects of the device, for example, the fact that it operates by measuring an impedance of an electromagnetic circuit extending partially inside and partially outside with respect to a protective layer. Furthermore, also when the part of the device, that is external with respect to the protective layer, is corroded, useful information about the actual state of corrosion can be obtained, and it is even possible to still provide functions of detection of the presence of water and of the acidity/basicity level.

Furthermore, the described system can be used to carry out measurements on fluids, for example inside tanks or chemical plants, or in the building material itself, before it solidifies to form the solid structure 300.

To the embodiments of the detecting device, and of the monitoring/detecting system and method described above, those skilled in the art, to meet contingent needs, will be able to make modifications, adaptations, and replacements of elements with other functionally equivalent ones, also combined to the prior art, creating, creating also hybrid implementations, without departing from the scope of the following claims. Each of the characteristics described as belonging to a possible embodiment can be implemented independently from the other embodiments described.

The invention claimed is:

1. An integrated electronic device for detecting changes in a parameter related to an environment surrounding the device, the device comprising:
   first and second conductive members;
   a measurement module comprising first and second measurement terminals respectively coupled to the first and the second conductive members, and configured to provide an electrical potential difference between the first and second conductive members;
   a separation layer comprising an insulating material and configured to enclose the first and second conductive members and the measurement module so as to be separated from the surrounding environment; and
   an electrode assembly on the separation layer and exposed to the surrounding environment and adjacent the first and the second conductive members, the electrode assembly forming with the first and second conductive members an electromagnetic circuit having an impedance that varies based upon exposure to the surrounding environment; and
   wherein the measurement module is configured to measure the impedance between the first and second measurement terminals to detect changes in the environmental parameter based on changes of the measured impedance, wherein the impedance is a complex number, wherein the device determines that an increase in a level of humidity of the surrounding environment has occurred in response to a decrease in an imaginary part of the impedance, wherein the device determines that an increase in the presence of water within the surrounding environment has occurred in response to a decrease in a real part of the impedance, and wherein the device determines that corrosion of a metal structure present within the surrounding environment has occurred in response to an increase in the real part of the impedance.

2. The device according to claim 1, wherein the insulating material comprises a passivation and galvanic insulation material.

3. The device according to claim 1, wherein the electrode assembly comprises a third conductive member to form with the first conductive member a first capacitor having a first capacitance, and to form with the second conductive member a second capacitor having a second capacitance so that the electromagnetic circuit comprises the first capacitor, the third conductive member and the second capacitor coupled in series, with the third conductive member having an external impedance associated therewith, and with the impedance of the electromagnetic circuit being defined by the first capacitance, the external impedance, and the second capacitance.

4. The device according to claim 2, wherein the third conductive member comprises a plurality of stripes comprising an electrically conductive material arranged on the separation layer so as to form a stripe geometric pattern comprising the plurality of stripes and a plurality of interstitial spaces between the plurality of stripes;
   wherein the stripe geometric pattern has a first portion overlapping the first conductive member and spaced apart therefrom by the separation layer; and
   wherein the stripe geometric pattern has a second portion overlapping the second conductive member and spaced apart therefrom by the separation layer.

5. The device according to claim 1, wherein the environment surrounding the device is solid material that includes metal structures.

6. The device according to claim 5, wherein the electrode assembly comprises a third conductive member comprising a plurality of stripes comprising an electrically conductive material arranged on the separation layer so as to form a stripe geometric pattern comprising the plurality of stripes and a plurality of interstitial spaces between the plurality of stripes, with the interstitial spaces to be filled by the solid material.

7. The device according to claim 5, wherein the solid material comprises concrete and the metal structures comprise metal rods within the concrete.

8. The device according to claim 1, further comprising an absorbing material on the electrode assembly exposed to the surrounding environment, the absorbing material comprising a dielectric and polymeric absorbing material to absorb humidity and/or water from the surrounding environment.

9. The device according to claim 8, wherein the electrode assembly comprises a third conductive member comprising a plurality of stripes comprising an electrically conductive material arranged on the separation layer so as to form a stripe geometric pattern comprising the plurality of stripes and a plurality of interstitial spaces between the plurality of stripes, with the absorbing material contacting both the separation layer and the third conductive member so as to fill interstitial spaces.

10. The device according to claim 1, wherein the first and second conductive members comprise conductive segments arranged in a shape of a double comb.

11. The device according to claim 1, wherein the first and second conductive members are separated by an internal insulating material that is not exposed to the surrounding environment.

12. The device according to claim 1, wherein the measurement module is configured to generate an alternating voltage with a preset frequency.

13. The device according to claim 1, wherein the measurement module comprises a processor configured to store initial calibration data, to perform measurements, to store the measurements, and to correlate differences between the stored initial calibration data and the measurements with changes in the environmental parameter.

14. A method for detecting changes in a parameter related to a surrounding environment, the method comprising:
   providing a device comprising:
      a measurement module comprising first and second measurement terminals respectively coupled to first and second conductive members respectively, and configured to provide an electrical potential difference between the first and second conductive members;
      a separation layer comprising an insulating material and configured to enclose the first and second conductive members and the measurement module so as to be separated from the surrounding environment; and
      an electrode assembly over the separation layer and exposed to the surrounding environment and adjacent the first and the second conductive members, the electrode assembly forming with the first and second conductive members an electromagnetic circuit having an impedance that varies based upon changes in the electrode assembly caused by exposure to the surrounding environment;
   operating the device so that the measurement module measures a reference impedance between the first and second measurement terminals;
   positioning the device within the surrounding environment; operating the device so that the measurement module measures an overall impedance between the first and second measurement terminals; and
   correlating deviation of the measured overall impedance from the measured reference impedance with changes in the environmental parameter, wherein the overall impedance is a complex number, and wherein correlating deviation of the measured overall impedance comprises:
   determining that an increase in a level of humidity of the surrounding environment has occurred in response to a decrease in an imaginary part of the overall impedance;
   determining that an increase in the presence of water within the surrounding environment has occurred in response to a decrease in a real part of the overall impedance; and
   determining that corrosion of a metal structure present within the surrounding environment has occurred in response to an increase in the real part of the overall impedance.

15. The method according to claim 14, wherein the electrode assembly comprises a third conductive member to form with the first conductive member a first capacitor having a first capacitance, and to form with the second conductive member a second capacitor having a second capacitance so that the electromagnetic circuit comprises the first capacitor, the third conductive member and the second capacitor coupled in series, wherein the third conductive member has an external impedance associated therewith, and wherein the overall impedance of the electromagnetic circuit is defined by the first capacitance, the external impedance, and the second capacitance.

16. The device according to claim 1, wherein changes in the impedance of the electromagnetic circuit result from changes in the electrode assembly caused by exposure to the surrounding environment.

\* \* \* \* \*